(12) United States Patent
Harman et al.

(10) Patent No.: US 9,822,334 B2
(45) Date of Patent: Nov. 21, 2017

(54) RAPID ACTING LACTOBACILLUS STRAINS AND THEIR USE TO IMPROVE AEROBIC STABILITY OF SILAGE

(71) Applicant: PIONEER HI BRED INTERNATIONAL INC, Johnston, IA (US)

(72) Inventors: Elizabeth Harman, Alleman, IA (US); William Rutherford, Grimes, IA (US); Brenda Smiley, Granger, IA (US)

(73) Assignee: PIONEER HI-BRED INTERNATIONAL, INC. IA (US)

(*) Notice: Subject to any disclaimer, the term of this patent is extended or adjusted under 35 U.S.C. 154(b) by 0 days.

(21) Appl. No.: 14/200,231

(22) Filed: Mar. 7, 2014

(65) Prior Publication Data

US 2015/0250207 A1  Sep. 10, 2015

(51) Int. Cl.
| | | |
|---|---|---|
| A23K 1/00 | (2006.01) |
| C12N 1/20 | (2006.01) |
| C12R 1/24 | (2006.01) |
| C12R 1/225 | (2006.01) |
| A23K 30/18 | (2016.01) |

(52) U.S. Cl.
CPC ............ *C12N 1/20* (2013.01); *A23K 30/18* (2016.05); *C12R 1/225* (2013.01); *C12R 1/24* (2013.01)

(58) Field of Classification Search
CPC .................................................. A23K 30/18
USPC ........................................................ 426/61
See application file for complete search history.

(56) References Cited

U.S. PATENT DOCUMENTS

| | | | |
|---|---|---|---|
| 4,820,531 A | 4/1989 | Tomes | |
| 4,842,871 A | 6/1989 | Hill | |
| 4,863,747 A | 9/1989 | Tomes | |
| 4,981,705 A | 1/1991 | Tomes | |
| 5,026,647 A | 6/1991 | Tomes et al. | |
| 5,292,657 A | 3/1994 | Rutherford et al. | |
| 5,725,853 A | 3/1998 | Dennis et al. | |
| 5,747,020 A | 5/1998 | Rutherford et al. | |
| 6,054,148 A | 4/2000 | Rust et al. | |
| 6,143,543 A | 11/2000 | Michelsen et al. | |
| 6,326,037 B1 * | 12/2001 | Mann et al. | 426/52 |
| 6,337,068 B1 | 1/2002 | Hendrick et al. | |
| 6,403,084 B1 * | 6/2002 | Chan et al. | 424/93.45 |
| 6,489,158 B1 | 12/2002 | Hendrick et al. | |
| 6,602,700 B1 | 8/2003 | Li et al. | |
| 6,699,514 B2 | 3/2004 | Mann | |
| 6,750,051 B2 | 6/2004 | Tricarico et al. | |
| 7,132,589 B2 | 11/2006 | Dunn-Coleman et al. | |
| 7,453,023 B2 | 11/2008 | Dunn-Coleman et al. | |
| 7,799,551 B2 | 9/2010 | Nsereko et al. | |
| 7,919,683 B2 | 4/2011 | Smiley et al. | |
| 2003/0024009 A1 | 1/2003 | Dunn-Coleman et al. | |
| 2004/0247568 A1 * | 12/2004 | Guerino et al. | 424/93.4 |
| 2006/0005270 A1 | 1/2006 | Dunn-Coleman et al. | |
| 2006/0046292 A1 | 3/2006 | Nsereko et al. | |
| 2008/0138461 A1 | 6/2008 | Chan et al. | |
| 2008/0138462 A1 | 6/2008 | Chan et al. | |
| 2008/0138463 A1 | 6/2008 | Chan et al. | |
| 2009/0010903 A1 | 1/2009 | Nsereko et al. | |
| 2009/0011085 A1 | 1/2009 | Nsereko et al. | |
| 2009/0028991 A1 | 1/2009 | Chan et al. | |
| 2009/0028992 A1 | 1/2009 | Chan et al. | |
| 2009/0028993 A1 | 1/2009 | Chan et al. | |
| 2011/0154533 A1 | 6/2011 | Smiley et al. | |

FOREIGN PATENT DOCUMENTS

| | | |
|---|---|---|
| EP | 0 880 323 B1 | 6/2001 |
| WO | 92/10945 A1 | 7/1992 |
| WO | 93/13786 A1 | 7/1993 |
| WO | 96/17525 A1 | 6/1996 |
| WO | 00/00040 A1 | 1/2000 |
| WO | 02/39825 A2 | 5/2002 |
| WO | 02/068666 A1 | 9/2002 |
| WO | 03/043411 A3 | 5/2003 |
| WO | 2006/007395 A1 | 1/2006 |
| WO | 2006/026763 A1 | 3/2006 |

OTHER PUBLICATIONS

Filya. J. Dairy Sci. 2003. 86: 3575-3581.*
Van Ransta, G., V. Fievezb, J. De Rieka, and E. Van Bockstaele. 2009. Influence of ensiling forages at different dry matters and silage additives on lipid metabolism and fatty acid composition. Anim. Feed Sci. Technol. 150:62-74.
Benton, J. R., T. Klopfenstein, and G. E. Erickson. 2005. Effects of corn moisture and length of ensiling on dry matter digestibility and rumen degradable protein. University of Nebraska. Nebraska Beef Cattle Reports: 31-33.
Cone, J. W., A. H. Van Gelder, H. A. Van Schoten, J. A. M. Groten. 2008. Effects of chop length and ensiling period of forage maize on in vitro rumen fermentation characteristics. Netherlands Journal of Agricultural Science. 55:155-166.

(Continued)

*Primary Examiner* — Hamid R Badr

(57) ABSTRACT

A method for treating silage to enhance the aerobic stability by increasing the fermentation and stabilization of silage by inhibiting growth of microorganisms selected from yeasts, molds and spore-forming bacteria and permitting earlier aerobic 5 exposure is disclosed. The method comprises treating silage or feed with a composition comprising *Lactobacillus buchneri* strain LN7125, or *Lactobacillus brevis* strain LB5328, or *Lactobacillus brevis* strain LB7123, and mixtures or a mutant thereof which retains the silage preservative activity of LN7125, LB5328, or LB7123, or the antimicrobial components produced thereby. The strains of *Lactobacillus* 10 *buchneri* and *Lactobacillus brevis* disclosed in the invention have been purified and isolated and have been found to improve aerobic stability of silage allowing earlier aerobic exposure post ensiling than is presently practiced.

6 Claims, No Drawings

(56) References Cited

OTHER PUBLICATIONS

Der Bedrosian, M. C., L. Kung, Jr., K. E. Nestor, Jr. 2010. The effects of length of storage on the composition and nutritive value of corn silage. J. Dairy Sci. 93 (Suppl. 1):176. Abstr.
Hallada, C. M., D. A. Sapienza, and D. Taysom. 2008. Effect of length of time ensiled on dry matter, starch and fiber digestibility in whole plant corn silage. J. Dairy Sci. vol. 91:E-Suppl.:30. Abstr.
Hoffman, P. C., N. M. Esser, R. D. Shaver, W. Coblentz, M.P. Scott, A.L. Bodnar, R. Schmidt, and B. Charley. 2010a. Influence of inoculation and storage time on alteration of the starch-protein matrix in high moisture corn. J. Dairy Sci. 93(Suppl. 1):726. Abstr.
Newbold, J. R., E. A. Lewis, J. Lavrijssen, H. J. Brand, H. Vedder, and J. Bakker. 2006. Effect of storage time on ruminal starch degradability in corn silage. J. Dairy Sci. 89(Suppl. 1):190. Abstr.
Schaadt, Jr., H., and R. R. Johnson. 1969. Effect of ensiling time on distribution and losses of nitrogen in corn silage treated with limestone and NPN. J. Anim Sci. 29:57-61.
Yahaya, M. S., A. Kimura, J. Harai, H. V. Nguyen, M. Kawai, J. Takahashi, and S. Matsuoka. 2001. Effect of length of ensiling on silo degradation and digestibility of structural carbohydrates of lucerne and orchardgrass. Anim. Feed Sci. Technol. 92:141-148.
DuPont Pioneer Press Release, "DuPont Pioneer Launches Inoculant and Feed Technology Offerings in 2016" Aug. 5, 2015. www.pioneer.com/home/site/about/news-media/news-releases.com.
Adesogan, A.T., "Improving Forage Quality and Animal Performance with Fibrolytic Enzymes," Florida Ruminant Nutrition Sympsoium, 2005, pp. 91-109.
Collins, Matthew D., et al. "Deoxyribonucleic Acid Homology Studies of Lactobacillus casei, *Lactobacillus paracasei*, sp. nov., subsp. *paracasei* and subsp. *tolerans*, and *Lactobacillus rhamnosus* sp. nov., comb. nov.," International Journal of Systematic Bacteriology, 1989, vol. 39(2), pp. 105-108.
Driehuis, et al., Grass and Forage Science, vol. 56, pp. 330-343 (2001).
Donaghy, et al., Appl Microbiol Biotechnol. Aug. 1998 50 (2): 257-260.
Erasmus, et al., "Effect of Yeast Culture Supplement on Production, Rumen Fermentation, and Duodenal Nitrogen Flow in Dairy Cows", J. Dairy Sci., (1992), 75:3056-3065.
Faulds, et al., "Purification and characterization of a ferulic acid esterase (FAE-III) from Aspergillus niger, specificity for the phenolic moiety and binding to microcrystalline cellulose", Microbiology, (1994) 140: 779-787.
Filya, I. et al., "The Effect of Lactobacillus buchneri and Lactobacilus plantarum on the Fermentation, Aerobic Stability, and Ruminal Degradability of Low Dry Matter Corn and Sorghum Silages," J. Dairy Sci., (2003), vol. 86 pp. 3275-3581.
Hill, J. et al., "Effect of inoculation of herbage prior to ensiling with Streptomyces achromogenes ISP 5028 on chemical composition of silage", Animal Feed Science and Technology (2001), vol. 89, pp. 83-96.
Holzer, M. et al., "The Role of Lactobacillus buchneri in Forage Preservation", Trends in Biotechnology, (2003) vol. 21 (6) pp. 282-287.
Jarvis, et al. Biomass and Bioenergy (1997) 12 (6), pp. 453-460.
Kleinschmit, D.H. and L. Kung, "a Meta-analysis of the Effects of Lactobaillus buchneri on the Fermentation and Aerobic Stability of Corn and Grass and Small Grain Silages", J. Dairy Sci., (2006) vol. 89(10) pp. 4005-4013.
Loc, Nguyen Thi, et al., "Cassava Root Silage for Crossbred Pigs Under Village Conditions in Central Vietnam", Livestock Research for Rural Development (1997) vol. 9(2) (12 pages printed from Internet Nov. 17, 2009). www.fao.org/ag/aga/agap/frg/feedback/lrrd/lrrd9/2/loc922.htm.
Moore, H.I., et al., "Silos and Silage", 85 pages from Internet Nov. 17, 2009) www.smallstock.info/reference/moore/silage.htm.
Nsereko, V. et al. "Influence of inoculating forage with lactic acid bacterial strains that produce ferulate esterase on ensilage and ruminal degradation of fiber", Animal Feed Science and Technology (2008) vol. 145, pp. 122-135.
Oba, et al. "Effects of Brown Midrib 3 Mutation in Corn Silage on Dry Matter Intake and Productivity of High Yielding Dairy Cows", J. Dairy Sci. (1999) 82: 135-142.
Ranjit, N.K. and L. Kung, "The Effect of Lactobacillus buchneri, Lactobacillus plantarum, or a Chemical Preservative on the Fermentation and Aerobic Stability of Corn Silage", J. Dairy Sci., (2000) vol. 83, pp. 526-535.
Schrag, J.D., and M. Cygler, "Lipases and a Hydrolase Fold", Methods in Enzymology (1997), vol. 284, pp. 35-107.
Tabka, M.G., et al. "Enzymatic saccharification of wheat straw for bioethanol production by a combined cellulase xylanase and feruloyl esterase treatment", Enzyme and Microbial Technology (2006) vol. 39, pp. 897-902.
Taylor, C.C., et al. "Lactobacillus buchneri and Enzymes Improves the Aerobic Stability of High Moisture Corn", J. Animal Sci. (2000), vol. 78 (Supp 1) p. 111, (Abstract 477).
Wang, Xiokun, et al., "Purification and Characterization of a Feruloyl Esterase from the Intestinal Bacterium Lactobacillus acidophilus", Applied and Environmental Microbiology (2004), vol. 70 (4) pp. 2367-2372.
Weinberg, Z.G., et al., "New Trends and Oppurtunities in the Development and Use of Inoculants for Silage", FEMS Microbiology Reviews, Elsevier, Amsterdam, vol. 19, No. 1, (1996) pp. 53-68.
Whiter, A.G., et al., "The Effect of a Dry or Liquid Application of Lactobacillus plantarum MTD1 on the Fermentationof Alfalfa Silage", J. Dairy Sci. (2001), vol. 84 pp. 2195-2202.
Wohlt, et al., "Effect of Yeast on Feed Intake and Performance of Cows Fed Diets Based on Corn Silage During Early Lactaion", J. Dairy Sci. (1998) 81: 1345-1352.
International Search Report for PCT/US2005/031489, dated Dec. 28, 2005.
International Search Report for PCT/US2015/017516, dated May 4, 2015.
International Preliminary Report on Patentability for PCT/US2015/017516, dated Sep. 22, 2016.

\* cited by examiner

RAPID ACTING LACTOBACILLUS STRAINS AND THEIR USE TO IMPROVE AEROBIC STABILITY OF SILAGE

FIELD OF THE INVENTION

The invention relates to compositions and methods of treating animal feed and preserving silage to enhance aerobic stability.

BACKGROUND OF THE INVENTION

The ensiling process is a method of moist forage preservation and is used worldwide. Silage accounts for more than 200 million tons of dry matter stored annually in Western Europe and the United States alone. The process involves natural fermentation, where lactic acid bacteria ferment water soluble carbohydrates to form organic acids under anaerobic conditions. This causes a decrease in pH which then inhibits detrimental microbes so that the moist forage is preserved.

Aerobic instability is the primary problem in silage production. Traditionally, the recommendation has been to allow silage to ferment for at least thirty (30) days before feeding to aid in increased silage digestibility. Even before storage units are open for feedout, silage can be exposed to oxygen because of management problems (i.e., poor packing or sealing). Under these types of aerobic conditions, rapid growth of yeast and mold cause silages to heat and spoil, decreasing its nutritional value. Feeding a crop that has not been properly fermented can lower dry matter intake (DMI), decrease milk production, and cause digestive upsets. Allowing time for adequate fermentation creates a more palatable and digestible feed for optimum DMI and milk production.

Aerobic instability can be a problem even in inoculated silage that has undergone what would traditionally be considered a "good" fermentation: a rapid pH drop, and a low terminal pH. The yeast organisms which contribute to instability in these conditions however may be those which are tolerant of acid conditions and can metabolize the lactic acid produced by lactic acid bacteria during fermentation.

It is possible to use both chemical and biological additives in making silage to promote adequate fermentation patterns especially under sub-optimal conditions. Typical chemical additives are most often organic acids and biological additives comprise bacterial inoculants and enzymes. Bacterial inoculants have advantages over chemical additives because they are safe, easy to use, non-corrosive to farm machinery, they do not pollute the environment and are regarded as natural products.

Production of silage inoculant strains and the ensiling process is complex and involves interactions of numerous chemical and microbiological processes. Different strains of even the same species do not have identical properties and vary in their fermentation and production characteristics. Further, different silages and different methods of ensiling present a variety of different needs. A continuing need exists in the art for improved compositions and methods to improve the aerobic stability of silage and increase the efficient production of ensiled animal feed.

The present invention provides novel strains of *L. buchneri* and *L. brevis* and superior combinations thereof for use as silage inoculants.

SUMMARY OF THE INVENTION

Embodiments of the invention include compositions for use as silage inoculants comprising silage quality preserving amounts of heterofermentative lactic acid bacteria species and mixtures or a mutant thereof, and a suitable carrier. The heterofermentive lactic acid bacteria compositions, isolated and purified, improve the aerobic stability of ensiled forage, increasing the fermentation and stabilization of silage to permit earlier aerobic exposure. Such compositions may include, but are not limited to, *Lactobacillus buchneri* strain LN7125 (hereafter LN7125), having Patent Deposit No. NRRL B-50733, or *Lactobacillus brevis* strain LB5328 (hereafter LB5328), having Patent Deposit No. NRRL B-50731, or *Lactobacillus brevis* strain LB7123 (hereafter LB7123), having Patent Deposit No. NRRL B-50732, and mixtures or a mutant thereof which retains the silage preservative activity of LN7125, LB5328, or LB7123, and carrier. Such compositions may comprise about $10^1$ to about $10^{11}$ viable organisms per gram wet weight of silage optionally about $10^2$ to about $10^7$ viable organisms per gram wet weight of silage, for example about $10^3$ to about $10^6$ viable organisms per gram wet weight of silage. The carrier in the compositions of the embodiments may be a liquid or a solid, such as, but not limited to, calcium carbonate, starch, and cellulose.

DETAILED DESCRIPTION OF THE INVENTION

The present invention now will be described more fully hereinafter with reference to the accompanying tables, in which some, but not all embodiments of the inventions are shown. Indeed, these inventions may be embodied in different modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

Units, prefixes, and symbols may be denoted in their SI accepted form. Numeric ranges recited within the specification are inclusive of the numbers defining the range and include each integer within the defined range.

The article "a" and "an" are used herein to refer to one or more than one (i.e., to at least one) of the grammatical object of the article. By way of example, "an element" means one or more elements.

As used herein, "animal performance" means the yield of meat, milk, eggs, offspring, or work.

As used herein, "ensiling" or "ensiled" refers to an anaerobic fermentation process used to preserve forages, immature grain crops, and other biomass crops for feed and biofuels. In some embodiments, the process of ensiling comprises the steps of contacting forage with a microbial inoculant and storing the mixture in an anaerobic condition. In certain embodiments, the process of ensiling comprises the steps of storing forage in anaerobic condition in a manner so as to exclude air. Forage, having been inoculated with the microbial inoculant described elsewhere herein, is also packed and stored in a manner so as to exclude air. The moisture content of forage can be about 50% to about 80%, depending on the means of storage, the amount of compression, and the expected moisture loss during storage. Ensiling can occur in silos, silage heaps, silage pits, silage bales, or any other method appropriate for ensiling the chosen plant material. Plant material with the microbial inoculant described elsewhere herein can be ensiled for any amount of time appropriate to produce silage at the desired maturity stage. In some embodiments, ensiling occurs for about 7, about 15, about 20, about 25, about 30, about 35, about 40, about 41, about 42, about 43, about 44, about 45, about 46, about 47, about 48, about 49, about 50, about 55, about 60, about 65, about 70 days, about 4 months, about 8 months, about 12 months, about 18 months, or about 24 months or any time period deemed suitable by the practitioner. The ensiling process can take place at any ambient temperature, for example at an ambient temperature from 0-45° C. The temperature of the plant material being ensiled may, however, increase above 45° C. Mature silage can be used for animal feed, frozen and stored for a later use, or added to a biogas generator for the production of biogas.

As used herein, "functional mutant" means a bacterial strain directly or indirectly obtained by genetic modification of, or using, the referenced strain(s) and retaining at least 50% of the activity of the referenced strain. The genetic modification can be achieved through any means, such as but not limited to, chemical mutagens, ionizing radiation, transposon-based mutagenesis, or via conjugation, transduction, or transformation using the referenced strains as either the recipient or donor of genetic material.

As used herein, the term "heterofermentative lactic acid bacteria species" shall be interpreted to include, but not limited to, *leuconostocs*, some *lactobacilli, oenococci*, and *weissella* species. Heterofermenters produce lactic acid, ethanol, acetic acid and carbon dioxide, with the proportions depending upon the substrates available.

As used herein, the term "homofermentative lactic acid bacteria species" shall be interpreted to include, but not limited to, some *lactobacilli* and most species of *enterococci, lactococci, pediococci, streptococci, tetragenococci*, and *vagococci* that ferment hexoses by the Embden-Meyerhof (E-M) pathway. Homofermentative denotes that lactic acid is the principal metabolite without the production of carbon dioxide. For each six carbon sugar molecule, homofermentative lactic acid bacteria will produce two molecules of lactic acid.

As used herein, "isolated" means removed from a natural source including, but not limited to, uninoculated silage or other plant material. As used herein, "microbial inoculant" refers to a composition comprising at least one bacterial culture and a suitable carrier. A "combination microbial inoculant" comprises at least 2, at least 3, at least 4, at least 5, at least 6, at least 7, or more bacterial cultures and a suitable carrier. Bacterial cultures comprise at least one bacterial strain and may comprise multiple bacterial strains, including for example, at least 2, at least 3, at least 4, at least 5, at least 6, at least 7, or more. Bacterial cultures useful in the methods and compositions disclosed herein include, but are not limited to, LN7125, LB5328, or LB7123.

As used herein, "pre-ensiled plant material" includes, but is not limited to, grasses, maize, alfalfa, wheat, ryegrass, cereals, oil seeds, sorghum, sunflower, barley and mixtures thereof prior to fermentation. All of which can be treated successfully with the inoculants of the embodiments of the present invention. The inoculants of the embodiments of the present invention are also useful in treating high moisture corn (HMC).

As used herein, "oilseeds" includes, but is not limited to sunflower, canola, soy, and mixtures thereof.

As used herein, "purified" means that a bacterial species or strain is substantially separated from, and enriched relative to: yeasts, molds, and/or other bacterial species or strains found in the source from which it was isolated.

The term "silage" as used herein is intended to include all types of fermented agricultural products, including but not limited to, grass silage, alfalfa silage, wheat silage, legume silage, sunflower silage, barley silage, whole plant corn silage (WPCS), sorghum silage, fermented grains and grass mixtures, etc.

As used herein, the term "strain" or "strain(s)" shall be interpreted to include, but not limited to, any mutant or derivative of the various bacterial strains disclosed herein, for example, *L. buchneri* strain LN7125, (Patent Deposit No. NRRL B-50733), or *L. brevis* strain LB5328, (Patent Deposit No. NRRL B-50731), or *L. brevis* strain LB7123, (Patent Deposit No. NRRL B-50732) which retains the functional activity of improving aerobic stability of forage as described and defined by the methods and examples disclosed herein.

Several microorganisms have been isolated and purified which improves the aerobic stability of ensiled forage, increasing the fermentation and stabilization of silage to permit earlier aerobic exposure. Specific strain(s) of the species *L. buchneri* or *L. brevis* have been shown to enhance aerobic stability of silage by not only reducing lactic acid levels but also by producing a substance which is inhibitory to microorganisms that contribute to causing aerobic instability in silage. While not wishing to be bound by any one theory, it is likely that a combination of metabolites is responsible for this effect. Furthermore, the metabolism of *L. buchneri* or *L. brevis* is believed to produce both acetic acid and propionic acid, both of which are known to inhibit the growth of yeast and molds.

The primary goal of ensiling forages is to conserve the maximum amount of original dry matter, nutrients and energy in the crop for feeding at a later time. The process can be characterized by four general phases of silage fermentation.

Upon sealing in the storage unit, the first phase is aerobic, when oxygen is still present between plant particles and the pH is 6.0 to 6.5. These conditions allow for continued plant respiration, protease activity and activity of aerobic and facultative aerobic microorganisms.

The second phase is fermentation, which lasts several days to several weeks after the silage becomes anaerobic. Lactic acid bacteria grow and become the primary microbial population thereby producing lactic and other organic acids, decreasing the pH to 3.8 to 5.0.

The third phase is stable with few changes occurring in the characteristics of the forage so long as air is prevented from entering the storage unit.

The final phase is feedout, when the silage is ultimately unloaded and exposed to air. This results in reactivation of aerobic microorganisms, primarily yeast, molds, bacilli and acetic acid bacteria which can cause spoilage.

Management techniques that can be used to help prevent this condition, include but are not limited to, using care to pack the silage well during the ensiling process, compaction, sealing, rapid filling, face management and, also, using care in removing silage for feeding to minimize the aeration of the remaining silage.

The susceptibility of silage to aerobic deterioration is determined by physical, chemical, and microbiological factors. Management (compaction, unloading rates) largely effects the movement of oxygen into silage. During feedout, air can penetrate up to 1 m behind the silage face so that exposure to oxygen is prolonged. Fermentation acids and pH inhibit the rate of microbial growth but spoilage rates are affected also by microbial numbers and the rate of aerobic microbial growth on available substrates.

Lactic acid bacteria (LAB) are present as part of the normal microflora on growing plants. LAB can be classified as one of two types depending upon their primary metabolic end products; homofermentative which produce only lactic acid from the metabolism of glucose and heterofermentative which produce lactic acid, ethanol, acetate and $CO_2$. The occurrences of these types are quite variable in both type and number, crop to crop and location to location.

Silage inoculants comprising principally homofermentative lactic acid bacteria have become the dominant additives in many parts of the world. Their function is to promote rapid and efficient utilization of a crop's water soluble carbohydrates resulting in intensive production of lactic acid and a rapid decrease in pH, thus minimizing dry matter losses. Inoculants may also improve animal performance. However, homofermentative inoculants often have a negative effect on aerobic stability due to the conservation of readily available substrates for spoilage organisms.

The concept of heterofermentative lactic acid bacteria in an inoculant has gained recent favor. The idea is that increased levels of undissociated volatile fatty acids, such as acetate, may inhibit other microbes that initiate aerobic deterioration. Heterofermenters produce lactic acid, ethanol, acetic acid and carbon dioxide, with the proportions depending upon the substrates available. The acetate produced may inhibit deleterious organisms in the silage. Additionally, heterofermenters, such as *Lactobacillus buchneri*, are capable of metabolizing lactic acid to acetate and 1,2 propanediol under anaerobic conditions. With such mechanisms, one sixth of the carbon is lost to carbon dioxide during fermentation of glucose and one third of the lactic acid carbon is lost during anaerobic conversion to acetic acid. However a small loss of 1% or perhaps up to 2% of the dry matter is easily offset by much larger losses by that spoilage action of aerobic microorganisms. Concerns with heterofermentative lactic acid bacteria include, but are not limited to, effects on animal performance as well as the identification of appropriate strains useful for the procedure. Different strains of even the same species do not have identical properties and vary in their fermentation characteristics.

Nilson (*Arch Microbiol.* (1956) 24: 396-411) found that the predominant LAB in silage are *Streptococci* and *Lactobacilli* with *L. plantarum* being the most frequent species. Gibson et. al (*J. Gen. Micro.* (1958) 24: 60-70) reported that *L. plantarum* and *L. acidophilus* were the dominant components of the homofermentative flora. Beck (*Landwirtschaftliche Forschung.* (1972) 27: 55-63) showed that even in grass silage where the epiphyte population was dominated by heterofermentative LAB, by day four of the ensiling process, 85% of the organisms present were homofermentative. Langston et. al. (*USDA Technical Bulletin* No. 1187 (1958)) has shown that the 69% of the isolates in mature silage were homofermentative. A shift is sometimes noted toward heterofermentative LAB in mature silage owing to their tolerance to low pH and high acetate concentrations. Szigeti (*Acta Almentaria.* (1979) 8: 25-40) found that the LAB flora at extremely low pH consisted mainly of *L. plantarum* and *L. brevis*. Grazia and Suzzi (*J. Appl. Bacteriol.* (1984) 56: 373-379) have shown that a strong sensitivity to pH 3.6 was observed among the heterofermentative LAB.

A review of the silage process and the use of inoculants can be found in Weinberg, ZNG. and Muck, RE. (1996) *FMS Microbiology Rev.* 19:53-68, Wilkinson, J. M. and Davies, D. R. (2012) *Grass and Forage Science* 68:1-19, and Muck, Richard E. (2013) *Agricultural and Food Science* 22:3-15 the disclosures of which is incorporated herein by reference.

In embodiments of the present invention, the inhibition of organisms responsible for spoilage is accomplished by treating the silage with organisms of the species *L. buchneri* or *L. brevis*, especially the strain(s) LN7125, LB5328, or LB7123 or with compositions comprising LN7125, LB5328, or LB7123 or closely related organisms, and as well by treatment with effective mutants or equivalents of LN7125, LB5328, or LB7123 and compositions comprising same.

An embodiment of the invention is a microbial inoculant comprising *Lactobacillus* species that will alter the fermentation and enhance stabilization of silage to allow earlier aerobic exposure post ensiling than is presently practiced. Currently it is the industry standard to recommend to allow a minimum of thirty (30) days and preferably sixty (60) days for inoculated silages to remain under anaerobic conditions to achieve the maximum benefit of the inoculant's ability to preserve and enhance aerobic stability of the stored forage. Often producers are unable to permit their silage to remain unopened for the recommended length(s) of time due to their individual limitations of available silage for feeding. An embodiment of the invention to set a target of less than thirty (30) days for anaerobic fermentation, in a sealed silage structure, with a *Lactobacillus* strain with or without a lactic acid bacteria (LAB) combination. A sealed silage structure may have a target for anaerobic fermentation of at least 29, 28, 27, 26, 25, 24, 23, 22, 21, 20, 19, 18, 17, 16, 15, 14, 13, 12, 11, 10, 9, 8, or 7 days.

An embodiment of the invention is a biologically pure culture of *L. buchneri* strain LN7125, having Patent Deposit No. NRRL B-50733, or *L. brevis* strain LB5328, having Patent Deposit No. NRRL B-50731, or *L. brevis* strain LB7123, having Patent Deposit No. NRRL B-50732.

A method of the embodiments is a method of treating animal feed or silage, comprising administering a silage inoculant comprising LN7125, LB5328, or LB7123 to the feed or silage at about $1 \times 10^3$ to $1 \times 10^6$ CFU/g of feed or silage. Additionally, another method of the embodiments is a method of improving animal performance, comprising feeding the animal the animal feed that has been inoculated with the silage inoculants as described in the other embodiments.

A further embodiment is a silage inoculant, comprising viable cultures of a homofermentive lactic acid bacteria and a heterofermentive lactic acid bacteria, see for example, U.S. Pat. No. 6,403,084. Additional embodiments include animal feed or silage comprising this silage inoculant.

Embodiments of the invention include methods for treating silage by inhibiting the growth thereon of spoilage organisms selected from yeasts, molds and spore-forming bacteria, which comprises: adding to the silage a spoilage organism inhibiting amount of the compositions of the embodiments. The silage to be treated by the methods of the embodiments may be made from a variety of plant sources, including but not limited to, grass, maize, alfalfa, wheat, rye grass, cereals, oil seeds, sorghum, sunflower and barley. The compositions of the embodiments may also be added to the silage upon storage. The silage may be ensiled in a variety of ways, including in the form of a bale, a bag, a bunker, a stave silo, or a pile. The methods of treating silage using the compositions of the embodiments include adding to the silage a silage quality preserving amount of LN7125, LB5328, or LB7123.

Embodiments of the invention further include silage comprising a silage quality preserving amount of LN7125, LB5328, or LB7123 or a silage quality preserving amount of a mutant thereof.

The silage included in the embodiments provides methods of treating silage for animal feed with the silage inoculant of the present invention, as well as the treated animal feed or silage itself. Often, the animal feed or silage will be whole plant corn silage (WPCS) or high moisture corn (HMC). The embodiments also provide a method of improving animal performance by feeding the inoculated silage. Containers comprising the silage inoculant of the present invention and a carrier are also included.

An embodiment of the invention is a method for improving aerobic stability of silage while also enhancing plant fiber digestion in an animal by feeding an effective amount of silage that has been inoculated with LN7125, LB5328, or LB7123 combined with a ferulate esterase-producing bacterial strain or a functional mutant thereof and a suitable carrier. Methods of using such ferulate esterase producing strains is disclosed in U.S. Pat. No. 7,799,551, herein incorporated by reference. The ferulate esterase strain may be, for example, a *Lactobacillus* strain or a functional mutant thereof, such as a *Lactobacillus* strain selected from the group consisting of *L. buchneri*, *L. plantarum*, *L. brevis*, *L. reuteri*, *L. alimentarius*, *L. crispatus*, and *L. paralimentarius*. Such strains may include, for example, those selected from the group consisting of *L. buchneri*, strain LN4017 (Patent Deposit No. PTA-6138), *L. plantarum*, strain LP678 (Patent Deposit No. PTA-6134), *L. plantarum*, strain LP3710 (Patent Deposit No. PTA-6136), *L. plantarum*, strain LP3779 (Patent Deposit No. PTA-6137), *L. plantarum*, strain LP7109 (Patent Deposit No. PTA-6139), *L. brevis*, strain LB1154 (Patent Deposit No. NRRL B-30865), *L. buchneri*, strain LN4888 (Patent Deposit No. NRRL B-30866), *L. reuteri*, strain LR4933 (Patent Deposit No. NRRL B-30867), *L. crispatus* LI2127 (Patent Deposit No. NRRL B-30868), *L. crispatus*, strain LI2350 (Patent Deposit No. NRRL B-30869), *L. crispatus*, strain LI2366 (Patent Deposit No. NRRL B-30870), *Lactobacillus* species unknown, strain UL3050 (Patent Deposit No. NRRL B-30871), and mixtures thereof (See U.S. Pat. No. 7,799, 551). Such compositions may include about $10^1$ to about $10^{10}$ viable organisms of the bacterial strains or functional mutants thereof per gram of a pre-ensiled plant material. Optionally, they may include from about $10^2$ to about $10^7$ viable organisms of the bacterial strains or functional mutants thereof, for example from about $10^3$ to about $10^6$ viable organisms of the bacterial strains or functional mutants thereof per gram of a pre-ensiled plant material.

The composition that is fed to the animal may be treated with an effective catalytic amount of the ferulate esterase producing bacterial strain or functional mutant thereof, as is readily determinable by those skilled in the art in animal husbandry. Animals that are benefited by embodiments of the present invention are mammals and birds, including but not limited to ruminant, equine, bovine, porcine, caprine, ovine and avian species, e.g., poultry.

The compositions which are used in the embodiments of the invention may be in either liquid or dry form and may comprise additional bacterial strains. In solid treatment forms, the composition may comprise mixed bacterial culture comprising LN7125, LB5328, or LB7123 together with a carrier. The carrier may be in the nature of an aqueous or nonaqueous liquid or a solid. In solid forms, the composition may comprise solid carriers, solid diluents or physical extenders. Examples of such solid carriers, solid diluents or physical extenders include maltodextrin, starches, calcium carbonate, cellulose, whey, ground corn cobs, and silicone dioxide. Liquid carriers may be solutions, without limitation, in the form of emulsifiable concentrates, suspensions, emulsion including microemulsions and/or suspoemulsions, and the like which optionally can be thickened into gels. In short, the carrier may be organic or an inorganic physical extender. The solid composition can be applied directly to the forage in the form of a light powder dusting, or if it is disbursed in a liquid carrier, it can successfully be sprayed on the forage.

Those of ordinary skill in the art will know of other suitable carriers and dosage forms, or will be able to ascertain such, using routine experimentation. Further, the administration of the various compositions can be carried out using standard techniques common to those of ordinary skill in the art. Another embodiment of the invention is the combination of LN7125, LB5328, or LB7123 with other specific bacterial species in the proper ratio to provide both an increase in fermentation and stabilization of silage or animal feed as well as an enhanced aerobic stability upon exposure of the silage or feed to air to allow for early aerobic exposure. The silage inoculant can be an isolated and purified combination of at least one viable strain of the homofermentative lactic acid bacteria *Lactobacillus plantarum* combined with the heterofermentive bacteria of LN7125, LB5328, or LB7123. In some embodiments, the silage inoculant will comprise at least 2 to 10 strains of homofermenter and/or heterofermenter. Exemplary strains of *L. plantarum* include at least one of LP286, LP287, LP329, LP346, LP347, or functional mutants thereof (see, for example, U.S. Pat. No. 6,403,084). Exemplary strains of *L. buchneri* which could be combined with LN7125, LB5328, or LB7123 include LN1391, LN4637, LN4750, or functional mutants thereof. The silage inoculant optionally comprises at least one viable strain of *Enterococcus faecium*, such as, but not limited to, strains EF301, EF202, or functional mutants thereof. The number of viable homofermentive bacteria and heterofermentive bacteria in the inoculant are present in a ratio of from about 1:5 to about 1:15. In some embodiments the ratio is about: 1:6 to 1:14, 1:7 to 1:13, 1:8 to 1:12, 1:9 to 1:11, or 1:10.

Methods of using mixed cultures for improving either fermentation or aerobic stability of silage are disclosed in U.S. Pat. No. 6,403,084, which is herein incorporated by reference.

An embodiment of the invention is a composition for use as a silage inoculant comprising LN7125, LB5328, or LB7123 or a functional mutant thereof and a suitable carrier. In an embodiment of the invention the composition contains from about $10^1$ to about $10^{10}$ viable organisms of the bacterial strain or functional mutant thereof per gram of a pre-ensiled plant material. In a further embodiment of the invention the composition contains from about $10^2$ to about $10^7$ viable organisms of the bacterial strain or functional mutant thereof per gram of a pre-ensiled plant material. In yet a further embodiment the composition contains from about $10^3$ to about $10^6$ viable organisms of the bacterial strain or functional mutant thereof per gram of a pre-ensiled plant material.

Materials that are suitable for ensiling or storage, according to the methods of the invention, are any which are susceptible to aerobic spoilage. The material will usually contain at least 25% by weight dry matter. Such materials include, but are not limited to, rye or traditional grass, maize, including high moisture corn, whole plant corn, alfalfa, wheat, legumes, cereals, oil seeds, sorghum, sunflower, barley or other whole crop cereals. The silage storage management includes, but is not limited to, in bales (a form particularly susceptible to aerobic spoilage), oxygen limiting bags, bunkers, upright stave silos, oxygen limiting silos, bags, piles or any other form of storage which may be susceptible to aerobic spoilage.

The activity associated with this invention may be found in other strains of L. buchneri, in other species of Lactobacillus, e.g. L. kefir, L. parakefir and L. parabuchneri, L. brevis, L. sake, L. curvatus, other species of homofermentative lactic acid bacteria and possibly also in other genera. This can be established by routine experimentation, on the basis of the information herein.

As used herein, the term "strain" or "strain(s)" shall be interpreted to include any mutant or derivative of the various bacterial strains disclosed herein, for example, L. buchneri strain LN7125, (Patent Deposit No. NRRL B-50733), or L. brevis strain LB5328, (Patent Deposit No. NRRL B-50731), or L. brevis strain LB7123, (Patent Deposit No. NRRL B-50732) which retains the functional activity of improving aerobic stability of forage as described and defined by the methods and examples disclosed herein.

The LN7125, LB5328, or LB7123 microorganism of the embodiments was purified and isolated from corn or the feces of corn-fed sheep. After much experimentation it was discovered from testing a collection of isolates.

After purification and isolation of the specific strain, taxonomic studies were done to identify the strain. It was identified as L. buchneri or L. brevis and given the prototype number LN7125, LB5328, or LB7123. According to the invention, these strain(s), compositions comprising these strain(s), or the factors produced by these strain(s), are used to treat forage materials.

Embodiments of the present invention are further defined in the following Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The disclosure of each reference set forth herein is incorporated herein by reference in its entirety.

Deposits

The Lactobacillus buchneri strain LN7125, Lactobacillus brevis strain LB5328 and Lactobacillus brevis strain LB7123 were deposited on Mar. 14, 2012, with the Agricultural Research Service (ARS) Culture Collection, housed in the Microbial Genomics and Bioprocessing Research Unit of the National Center for Agricultural Utilization Research (NCAUR), under the Budapest Treaty provisions. The strain(s) were given Patent Deposit No. NRRL B-50733, Patent Deposit No. NRRL B-50731, and Patent Deposit No. NRRL B-50732, respectively. The address of NCAUR is 1815 N. University Street, Peoria, Ill., 61604. The deposit(s) will irrevocably and without restriction or condition be available to the public upon issuance of a patent. However, it should be understood that the availability of a deposit does not constitute a license to practice the subject invention in derogation of patent rights granted by government.

Applicant(s) will meet all the requirements of 37 C.F.R. §§1.801-1.809, including providing an indication of the viability of the sample when the deposit(s) is made. Each deposit will be maintained without restriction in the NRRL Depository, which is a public depository, for a period of 30 years, or 5 years after the most recent request, or for the enforceable life of the patent, whichever is longer, and will be replaced if it ever becomes nonviable during that period. The deposits will irrevocably and without restriction or condition be available to the public upon issuance of a patent. However, it should be understood that the availability of a deposit does not constitute a license to practice the subject invention in derogation of patent rights granted by government action.

All publications and patent applications mentioned in the specification are indicative of the level of those skilled in the art to which this disclosure pertains. All publications and patent applications are herein incorporated by reference to the same extent as if each individual publication or patent application was specifically and individually indicated to be incorporated by reference. Although the foregoing invention has been described in some detail by way of illustration and example for purposes of clarity of understanding, it will be obvious that certain changes and modifications may be practiced within the scope of the appended claims.

EXAMPLES

Example 1

Rapid Acting Lactobacillus Strains for Improving Silage Aerobic Stability in Corn Studies were performed to develop a microbial inoculant comprising Lactobacillus species that can increase the fermentation and stabilization of whole plant corn silage to allow for early opening (aerobic exposure) at less than thirty (30) days post-ensiling.

Strain Selection:

Heterofermentative lactic acid bacterial cultures (252 isolates), taken from Pioneer Hi-Bred's microbial culture collection, were grown in De Man Rogosa Sharpe broth (MRS broth; Difco™ Lactobacilli MRS; Becton Dickinson and Company, Sparks, Md. 21152 USA), prepared as described by the manufacturer, for 24 to 48 hours. An aliquot of cell suspension was transferred to an extract of whole plant corn forage broth (1:10 mixture of dried ground corn forage in water, autoclaved, 0.2 micron filter sterilized then 0.5% glucose added) and grown for 40 hours at 37 C.

After an initial screening process, five isolates were selected for field testing in 2011 to evaluate their ability to enhance the aerobic stability of ensiled whole plant corn forage. Strains were discovered and identified from corn or the feces of corn fed sheep samples taken in the United States. In 2012, three of the isolates were repeated in whole plant corn and in combination with commercial homofermentative strains LP286 and LP329.

Field Testing:
Test Strain Characteristics:

| Strain | 16S rDNA Species ID | Source | MRS gas production |
|---|---|---|---|
| LB7123 | Lactobacillus brevis | Sheep feces fed WPCS, Polk City, IA, 2008 | gas positive |
| LB4616 | Lactobacillus brevis | HMC, Dallas Center, 1997 | gas positive |
| LB5328 | Lactobacillus brevis | WPCS, IA, 1995 | gas positive |
| LB31 | Lactobacillus brevis | WPCS, Kersey, CO, 1993 | gas positive |
| LN7125 | Lactobacillus buchneri | WPCS, Polk City, IA, 2008 | gas positive |

Field Testing:

2011 Corn Harvest: Three hybrids (P1162, 33M16, DeKalb 61669vt3) of whole plant corn forage were individually harvested Sep. 1, 2011 at the Livestock Nutrition Center In Sheldahl, Iowa at a dry matter range of 33-37%.

2012 Corn Harvest: Three hybrids (P90115XR, P1162XR, P1395XR) of whole plant corn forage were individually harvested Sep. 21, 2012 at the Livestock Nutrition Center In Sheldahl, Iowa at a dry matter range of 33-37%.

2011 Corn Silage Treatments:

| Commercial Pioneer ® brand Whole Plant Corn Inoculants | Experimental Test Strains |
|---|---|
| 11A44 | LB31 |
| 1132 | LB4616 |
| 11C33 | LB5328 |
| 11CFT | LB7123 |
|  | LN7125 |

2012 Corn Silage Treatments:

| Commercial Pioneer ® brand Whole Plant Corn Inoculants | Experimental Test Strains & Combinations |
|---|---|
| 11A44 | LB5328 |
| 1132 | LB7123 |
| 11C33 | LN7125 |
| 11CFT | LB5328 + LP286 + LP329 |
|  | LB7123 + LP286 + LP329 |
|  | LN7125 + LP286 + LP329 |

Inoculation:

In 2011, individual experimental test strains were grown and supplied as fresh grown culture. In 2012, individual experimental test strains were grown, lyophilized in-house and supplied as dry powder culture. Commercial and experimental lyophilized products were suspended in water then all treatments were adjusted to a standard concentration of $4.54 \times 10^7$. Treatments suspensions were applied using a 10-cc syringe at a rate of 1.0 ml/lb of forage. The application dose for all treatments was $1 \times 10^5$ CFU/g forage.

Silos:

PVC silos were filled with 160 kg DM/m$^3$ of whole plant corn forage and air infused for 24 hours as described below based on opening days.

| Silo Opening Day | 24 hr Air Infusion Day |
|---|---|
| 7 | 0 |
| 14 | 7 |
| 28 | 14 |
| 60 | 45 |

Aerobic Stability: The method of Honig (Proc. Of the Eurobac. Conf., P. Lingvall and S. Lindgren (ed.) (12-16 August 1986) Swed. Univ. of Agric. Sci. Grass and Forage Report No. 3-1990. Pp. 76-81. Uppsala, Sweden.) used for measuring aerobic stability. Aerobic dry matter losses (DML) were estimated from the rise in temperature after exposure to air as described by Honig.

Results and Discussion

Aerobic Stability

Treatments with heterofermentative lactobacillus decrease the aerobic dry matter loss and increase the time to heating. Differences were observed between strains over time.

2011—Corn Silage (Table 1)

Opening at days 7 and 14 resulted in statistical differences between treatments LB5328, LB7123 and LN7125 and uninoculated control silage which held until day 60 when numerical effects were observed.

Treatment with LB5328, LB7123 and LN7125 also resulted in a statistical improvement over the current commercial inoculants (11A44, 11C33 and 11CFT) when evaluated at early opening times. These three strains show marked improvement over other selected heterofermentative strains (LB31 and LB4616). Two Lactobacillus brevis (LB7123 & LB5328) and one Lactobacillus buchneri (LN7125) selected from these studies were efficacious in improving aerobic stability of whole plant corn silage when opened prior to day 30 (days 7 and 14). Obvious differences from control and less efficacious strains were noted. The three strains were advanced for inclusion in the 2012 whole plant corn silage trials to be tested individually and in combination with current commercial homofermentative strains LP286 and LP329.

2012—Corn Silage (Table 2)

Opening on days 7 and 14, resulted in biological and statistical differences between single strain treatment LB7123 and uninoculated control silage. The differences at day 28 & 60 were numerically but not statistically better between LB7123 and control.

There was a continuing trend for the combination treatments of LB5328+, LB7123+, and LN7125+responding positively on day 7 and 14. Day 7 opening resulted in a numerical improvement in aerobic DML over control while the combination treatments were significantly better than control at day 14. All three combination treatments maintained the improvement (30-40%) over control. Similar improvement in aerobic dry matter losses were observed with 11A44 and 11CFT. The commercial products did not seem to be actively improving DML on days 7, 14 or 28; however, 11A44 and 11CFT had a positive impact on aerobic stability at day 60, as observed in previous research trials.

2011 & 2012 Combined Corn Silage Studies—(Table 3)

In general, the performance of single strain treatments LB5328, LB7123 and LN7125 over two years of whole plant corn silage trials (6 studies, 24 silos/tmt), was consistent in reducing aerobic dry matter loss over uninoculated control silage and current commercial products at openings before 28 days.

Treatments LB7123 and LN7125 were statistically better than control and commercial treatments at day 7 and 14. LN7123, LN7125 and LN7125 also demonstrated statistical differences from control by day 14. By day 28 & 60, these three single strains were numerically better than control and showed aerobic stability equivalent to commercial products 11A44, 11C33 and 11CFT.

Summary

Because of the reduced aerobic dry matter loss afforded by these strains and the combinations with homofermentors, repeatable improvements in dry matter losses are observed at early opening of ensiled whole plant forages providing an economic advantage to the producer using specifically selected *L. buchneri* or *L. brevis* inoculants.

TABLE 1

Effect of *Lactobacillus buchneri* and *Lactobacillus brevis* on dry matter losses upon exposure to air in whole plant corn silage ensiled for various lengths of time.

| 2011 | DMLoss-Days post-ensiling | | | |
|---|---|---|---|---|
|  | 7 | 14 | 28 | 60 |
| Control | $3.36^a$ | $5.73^a$ | $4.93^a$ | $4.37^{ab}$ |
| 1132 | $2.74^a$ | $5.22^a$ | $2.91^{bc}$ | $5.77^a$ |
| 11A44 | $3.71^a$ | $5.76^a$ | $3.19^{abc}$ | $5.39^{ab}$ |
| 11C33 | $2.99^a$ | $5.39^a$ | $4.26^{ab}$ | $4.57^{ab}$ |
| 11CFT | $2.29^{ab}$ | $4.75^{ab}$ | $3.14^{abc}$ | $4.39^{ab}$ |
| LB31 | $2.09^{abc}$ | $5.41^a$ | $3.52^{abc}$ | $5.09^{ab}$ |
| LB4616 | $2.12^{abc}$ | $4.41^{abc}$ | $3.17^{abc}$ | $5.04^{ab}$ |
| LB5328 | $1.95^{abc}$ | $3.23^{bc}$ | $2.40^c$ | $3.88^{ab}$ |
| LB7123 | $0.94^{bc}$ | $3.32^{bc}$ | $2.67^{bc}$ | $3.95^b$ |
| LN7125 | $0.51^{bc}$ | $2.99^c$ | $2.14^c$ | $3.95^b$ |

TABLE 2

Effect of *Lactobacillus buchneri*, *Lactobacillus brevis* and combinations with homofermentors on dry matter losses upon exposure to air in whole plant corn silage ensiled for various lengths of time.

| 2012 | DMLoss-Days post-ensiling | | | |
|---|---|---|---|---|
|  | 7 | 14 | 28 | 60 |
| Control | $2.91^{ab}$ | $4.66^a$ | $2.90^b$ | $2.95^a$ |
| 1132 | $2.94^{ab}$ | $4.17^{ab}$ | $2.97^b$ | $2.35^{ab}$ |
| 11A44 | $3.60^a$ | $3.60^{abcd}$ | $2.95^b$ | $1.03^b$ |
| 11C33 | $2.99^{ab}$ | $3.89^{abc}$ | $4.09^{ab}$ | $2.70^a$ |
| 11CFT | $3.46^a$ | $4.45^a$ | $4.72^a$ | $1.55^{ab}$ |
| LB5328 | $2.91^{ab}$ | $3.37^{abcd}$ | $3.89^{ab}$ | $2.39^{ab}$ |
| LB7123 | $0.95^c$ | $2.54^{de}$ | $2.77^b$ | $2.52^a$ |
| LN7125 | $2.20^b$ | $3.39^{abcd}$ | $3.32^{ab}$ | $2.28^{ab}$ |
| LB5328 + LP286 + LP329 | $2.76^{ab}$ | $2.80^{bcde}$ | $2.82^b$ | $2.02^{ab}$ |
| LB7123 + LP286 + LP329 | $2.20^b$ | $1.85^e$ | $3.31^{ab}$ | $1.86^{ab}$ |
| LN7125 + LP286 + LP329 | $2.03^{bc}$ | $2.70^{cde}$ | $2.50^b$ | $1.74^{ab}$ |

TABLE 3

Effect of *Lactobacillus buchneri* and *Lactobacillus brevis* on dry matter losses upon exposure to air in whole plant corn silage ensiled for various lengths of time.

| 2011 & 2012 Combined | DMLoss-Days post-ensiling | | | |
|---|---|---|---|---|
|  | 7 | 14 | 28 | 60 |
| Control | $3.10^{ab}$ | $5.02^a$ | $3.77^{ab}$ | $3.66^a$ |
| 11A44 | $3.76^a$ | $4.72^a$ | $2.98^{ab}$ | $3.31^a$ |

TABLE 3-continued

Effect of *Lactobacillus buchneri* and *Lactobacillus brevis* on dry matter losses upon exposure to air in whole plant corn silage ensiled for various lengths of time.

| 2011 & 2012 Combined | DMLoss-Days post-ensiling | | | |
|---|---|---|---|---|
|  | 7 | 14 | 28 | 60 |
| 11C33 | $2.99^{ab}$ | $4.67^a$ | $4.17^a$ | $3.63^a$ |
| 11CFT | $2.87^{ab}$ | $4.44^{ab}$ | $3.77^{ab}$ | $3.03^a$ |
| LB5328 | $2.43^b$ | $3.5613^c$ | $3.00^{ab}$ | $3.66^a$ |
| LB7123 | $0.94^c$ | $2.82^c$ | $2.72^b$ | $3.20^a$ |
| LN7125 | $1.35^c$ | $3.08^c$ | $2.64^b$ | $3.33^a$ |

Example 2

Rapid Acting *Lactobacillus* Strains for Improving Silage Aerobic Stability in Grasses Strain Selection:

Heterofermentative lactic acid bacterial cultures (252 isolates), taken from Pioneer Hi-Bred's microbial culture collection, were grown in De Man Rogosa Sharpe broth (MRS broth; Difco™ Lactobacilli MRS; Becton Dickinson and Company, Sparks, MD 21152 USA), prepared as described by the manufacturer, for 24 to 48 hours. An aliquot of cell suspension was transferred to an extract of whole plant corn forage broth (1:10 mixture of dried ground corn forage in water, autoclaved, 0.2 micron filter sterilized then 0.5% glucose added) and grown for 40 hours at 37C.

Strains were discovered and identified from corn or the feces of corn fed sheep samples taken in the United States. In 2012, three of the isolates were tested in European rye grass, and in 2013 only two isolates were tested as single strains and in combination with current commercial homofermentative strains LP286 and LP329.

Experimental Test Strain Characteristics:

| Strain | 16S rDNA Species ID | Source | MRS gas production |
|---|---|---|---|
| LB7123 | *Lactobacillus brevis* | Sheep feces fed WPCS, Polk City, IA, 2008 | gas positive |
| LB5328 | *Lactobacillus brevis* | WPCS, IA, 1995 | gas positive |
| LN7125 | *Lactobacillus buchneri* | WPCS, Polk City, IA, 2008 | gas positive |

Field Testing:

2012 Grass Harvest: European rye grass harvested around Buxtehude, Germany on May 22, 23, & 24, 2012 at a dry matter range of 33-49%.

2013 Grass Harvest: European rye grass harvested around Buxtehude, Germany on Jun. 3, 4 & 6, 2013 at a dry matter range of 36-46%.

2012 European Rye Grass Silage Treatments:

| Commercial Pioneer ® brand Grass Inoculants | Experimental Test Strains |
|---|---|
| 11A44 | LB5328 |
| 11G22 | LB7123 |
| 11GFT | LN7125 |

2013 European Rye Grass Silage Treatments:

| Commercial Pioneer ® brand Whole Plant Corn Inoculants | Experimental Test Strains & Combinations |
|---|---|
| 11A44<br>11GFT | LB7123<br>LN7125<br>LB7123 + LP286 + LP329<br>LN7125 + LP286 + LP329 |

Inoculation:

In 2012 & 2013, individual experimental test strains were grown, lyophilized in-house and supplied as dry powder culture. Commercial and experimental lyophilized products were suspended in water then all treatments were adjusted to a standard concentration of $4.54 \times 10^7$. Treatments suspensions were applied using a 10-cc syringe at a rate of 1.0 ml/lb of forage. The application dose for all treatments was $1 \times 10^5$ CFU/g forage.

Silos:

PVC silos were filled with 100 kg DM/m³ of grass and air infused for 24 hours as described below based on opening days.

| Silo Opening Day | 24 hr Air Infusion Day |
|---|---|
| 7 | 0 |
| 14 | 7 |
| 28 | 14 |
| 60 | 45 |

Aerobic Stability: The method of Honig (Proc. Of the Eurobac. Conf., P. Lingvall and S. Lindgren (ed.) (12-16 Aug. 1986) Swed. Univ. of Agric. Sci. Grass and Forage Report No. 3-1990. Pp. 76-81. Uppsala, Sweden.) used for measuring aerobic stability. Aerobic dry matter losses (DML) were estimated from the rise in temperature after exposure to air as described by Honig.

Results and Discussion:

Aerobic Stability

Treatments with heterofermentative lactobacillus decreased the aerobic dry matter loss and increased the time to heating. Differences were observed between strains over time.

2012—Grass Silage (Table 1)

Opening grass silos at day 14, 28 and 60 resulted in differences between single strain treatments LB5328, LB7123 and LN7125 and uninoculated control silage. These three treatments at days 7, 14 and 28 were numerically better than control and commercial products.

The commercial products did not appear to reduce aerobic DML on days 7 or 14; however, by day 28 11A44 and 11G22 were significantly improved over control. By day 60, with the exception of 11 GFT, all treatments were statically improved over control.

2013—Grass Silage (Table 2)

Single strain treatments LN7125 and LB7123 resulted in a considerable reduction in the aerobic dry matter loss when compared to uninoculated control across all opening days tested. The combination of LB7123 and the *L plantarum* strains was effective at reducing aerobic dry matter losses across all days while the *L. plantarum* combinations with LN7125 was not statistically different than the uninoculated control.

The commercial products had little effect on the aerobic dry matter loss until day 90 post-ensiling. Treatment with 11A44 was more effective at reducing the dry matter losses than was the combination product 11 G22.

Summary

Because of the reduced aerobic dry matter loss afforded by these strains and the combinations with homofermentors, repeatable improvements in dry matter losses were observed at early opening of ensiled grass forages providing an economic advantage to the producer using specifically selected *L. buchneri* or *L. brevis* inoculants.

TABLE 1

2012 Effect of *Lactobacillus buchneri* and *Lactobacillus brevis* on dry matter losses upon exposure to air in European grass silage ensiled for various lengths of time.

| 2012 European | DMLoss-Days post-ensiling | | | |
|---|---|---|---|---|
| Grass | 7 | 14 | 28 | 60 |
| Control | $2.76^{ab}$ | $7.10^a$ | $6.5^a$ | $3.30^a$ |
| 11A44 | $2.27^{abc}$ | $4.3^{ab}$ | $2.72^b$ | $1.18^b$ |
| 11G22 | $3.25^a$ | $6.35^a$ | $2.31^b$ | $0.00^b$ |
| 11GFT | $2.5^{ab}$ | $6.05^a$ | $6.07^a$ | $3.42^a$ |
| LB5328 | $1.68^{abc}$ | $2.41^b$ | $2.72^b$ | $0.77^b$ |
| LB7123 | $0.29^c$ | $2.47^b$ | $1.58^b$ | $0.01^b$ |
| LN7125 | $0.75^{bc}$ | $2.34^b$ | $2.02^b$ | $0.11^b$ |

$^{abc}$within a day, values with different superscript differ $p \leq 0.05$.

TABLE 2

2013 Effect of *Lactobacillus buchneri* and *Lactobacillus brevis* alone and in combination with *Lactobacillus plantarum* on dry matter losses upon exposure to air in European grass silage ensiled for various lengths of time.

| 2013 European | DMLoss-Days post-ensiling | | | |
|---|---|---|---|---|
| Grass | 7 | 14 | 28 | 90 |
| Control | $7.11^a$ | $6.46^{ab}$ | $6.08^{ab}$ | $1.77^a$ |
| 11A44 | $3.54^{abc}$ | $2.63^{bcd}$ | $0.22^c$ | $0.10^a$ |
| 11GFT | $5.77^{ab}$ | $7.56^a$ | $7.44^a$ | $1.46^a$ |
| LB7123 | $0.00^c$ | $0.23^d$ | $0.00^c$ | $0.00^a$ |
| LN7125 | $1.25^{ab}$ | $1.35^{cd}$ | $0.11^c$ | $0.00^a$ |
| LN7125 + LP286 + LP329 | $6.18^a$ | $5.24^{abc}$ | $3.52^{bc}$ | $0.17^a$ |
| LB7123 + LP286 + LP329 | $0.44^c$ | $1.08^{cd}$ | $2.58^{bc}$ | $0.46^a$ |

$^{abcd}$within a day, values with different superscript differ $p \leq 0.05$.

Having illustrated and described the principles of the embodiments of the present invention, it should be apparent to persons skilled in the art that the embodiments of the invention can be modified in arrangement and detail without departing from such principles. Thus, the invention encompasses all alternate embodiments that fall literally or equivalently within the scope of these claims.

It is understood that various preferred embodiments are shown and described above to illustrate different possible features of the invention and the varying ways in which these features may be combined. Apart from combining the different features of the above embodiments in varying ways, other modifications are also considered to be within the scope of the invention.

All publications and published patent documents cited in this specification are incorporated herein by reference to the same extent as if each individual publication or published patent document was specifically and individually indicated to be incorporated by reference.

What is claimed is:

1. A method for producing a fermented silage with increased aerobic stability comprising:
   adding to pre-ensiled plant material a silage preserving amount of the bacteria *Lactobacillus buchneri* LN7125, or *Lactobacillus brevis* LB5328, or *Lactobacillus brevis* LB7123, or mixtures thereof;
   placing the pre-ensiled plant material into a storage unit;
   sealing the storage unit to substantially limit contact with outside air to create a sealed storage unit;
   fermenting the silage anaerobically in the sealed storage unit for a period of at least seven days; and
   opening the sealed storage unit after a period of at least seven days; wherein the increased aerobic stability is compared to the aerobic stability of a silage without said bacteria as measured by dry weight loss.

2. A method according to claim 1, wherein the plant material is any one of: grass, maize, alfalfa, wheat, legumes, oilseeds, or sorghum.

3. A method according to claim 1, which comprises storing the treated plant material for twenty-nine (29) days.

4. A method according to claim 1, which comprises storing the treated plant material for twenty-eight (28) days.

5. A method according to claim 1, which comprises storing the treated plant material for fourteen (14) days.

6. A method according to claim 1, which comprises storing the treated plant material for seven (7) days.

* * * * *